United States Patent
Yang et al.

(10) Patent No.: US 10,788,408 B2
(45) Date of Patent: Sep. 29, 2020

(54) METHOD FOR DETERMINING DIFFUSION RADIUS OF IN-SITU INJECTION AND REMEDIATION OF CONTAMINATED SOIL AND GROUNDWATER

(71) Applicant: BCEG ENVIRONMENTAL REMEDIATION CO.,LTD, Beijing (CN)

(72) Inventors: Yuewei Yang, Beijing (CN); Shupeng Li, Beijing (CN); Yue Zhang, Beijing (CN); Xiaobin Zhang, Beijing (CN); Lili Guo, Beijing (CN); Shuangchao Cui, Beijing (CN); Xiaowei Song, Beijing (CN); Fan Chen, Beijing (CN); Pengcheng Yin, Beijing (CN); Peng Liu, Beijing (CN); Yan Liu, Beijing (CN); Qiang Niu, Beijing (CN)

(73) Assignee: BCEG Environmental Remediation Co., Ltd, Beijing (CN)

( * ) Notice: Subject to any disclaimer, the term of this patent is extended or adjusted under 35 U.S.C. 154(b) by 1 day.

(21) Appl. No.: 16/306,864

(22) PCT Filed: May 16, 2017

(86) PCT No.: PCT/CN2017/084471
§ 371 (c)(1),
(2) Date: Dec. 3, 2018

(87) PCT Pub. No.: WO2017/219791
PCT Pub. Date: Dec. 28, 2017

(65) Prior Publication Data
US 2019/0120741 A1  Apr. 25, 2019

(30) Foreign Application Priority Data

Jun. 23, 2016  (CN) .......................... 2016 1 0461743

(51) Int. Cl.
*G01N 13/00* (2006.01)
*E21D 1/00* (2006.01)
(Continued)

(52) U.S. Cl.
CPC ............... *G01N 13/00* (2013.01); *B09C 1/00* (2013.01); *B09C 1/002* (2013.01); *B09C 1/08* (2013.01);
(Continued)

(58) Field of Classification Search
None
See application file for complete search history.

(56) References Cited

U.S. PATENT DOCUMENTS

| 7,845,883 B1 | 12/2010 | Siler, III et al. |
| 2019/0391065 A1* | 12/2019 | Karazincir ............. G01N 33/24 |

FOREIGN PATENT DOCUMENTS

| CN | 103480645 | 1/2014 |
| CN | 103894409 | 7/2014 |

(Continued)

*Primary Examiner* — Richard C Gurtowski
(74) *Attorney, Agent, or Firm* — Muncy, Geissler Olds & Lowe, P.C.

(57) ABSTRACT

A method for determining the diffusion radius of in-situ injection and remediation of contaminated soil and groundwater. According to the triangle method, the hole spacing is perpendicular to the groundwater flow direction, the row spacing is along the groundwater flow direction, and the flow diffusion in the groundwater during the effective time of the remediation agent reaction is considered. Under high pressure rotary injection, the remediation agent and a certain proportion of bromide ions are simultaneously injected into the aquifer as a tracer. The diffusion of the agent is determined by observing the phenomenon of slurry-returning and slurry-channeling of adjacent injection points. After the completion of the injection, the groundwater is quickly sampled in fixed depth, the tracer concentration is quickly (Continued)

detected on site, and the concentration of bromide ions in the groundwater is compared with the background value. Comprehensive determination determines the optimal diffusion radius.

2 Claims, 4 Drawing Sheets

(51) Int. Cl.
*B09C 1/00* (2006.01)
*B09C 1/08* (2006.01)
*G01N 33/24* (2006.01)
*E21B 47/11* (2012.01)

(52) U.S. Cl.
CPC ............... *E21D 1/00* (2013.01); *G01N 33/24* (2013.01); *B09C 2101/00* (2013.01); *E21B 47/11* (2020.05); *G01N 2013/003* (2013.01)

(56) References Cited

FOREIGN PATENT DOCUMENTS

| | | |
|---|---|---|
| CN | 103934264 | 7/2014 |
| CN | 105973759 A | 9/2016 |

\* cited by examiner

METHOD FOR DETERMINING DIFFUSION RADIUS OF IN-SITU INJECTION AND REMEDIATION OF CONTAMINATED SOIL AND GROUNDWATER

TECHNICAL FIELD

The present invention relates to a method for determining the diffusion radius of in-situ injection and remediation of contaminated soil and groundwater, belong to the technical field of remediation and monitoring method for contaminated soil and groundwater.

BACKGROUND TECHNOLOGY

Groundwater contamination and remediation have received much attention in recent years. Many in-situ remediation technologies for groundwater, such as permeable reactive barrier (PRB), pump-& treatment, in-situ chemical remediation, and in-situ microbial remediation, have been applied domestically. The in-situ injection technology has lower energy consumption than the mixing technology, and thus is more widely used, especially in the field of groundwater remediation. The good permeability of the aquifer is beneficial to the addition of a highly water-soluble remediation agent. The important reason for the in-situ remediation technology being favored is that it can solve the problem of deep soil and groundwater contamination, avoiding problems such as deep foundation pit excavation, precipitation and secondary pollution, and greatly improving safety and economy.

The determination and optimal design of the effective diffusion radius of the remediation agent is the primary task in in situ injection remediation (in situ chemical oxidation/reduction, in situ microbial remediation). The effective diffusion radius ($R_0$) is one of the most important technical parameters of engineering design. Whether the design is reasonable or not directly affects the success or failure of the remediation project. If the value is designed to be too large, the remediation area cannot be completely covered, resulting in remediation "dead angle". If the value is designed to be too small, serious slurry-returning is caused, greatly increasing mechanical cost.

The determination of the radius of the grouting field (such as rotary jet grouting pile) is generally carried out by field test excavation or by technical tests such as drilling machine coring method, static penetration test and ultrasonic testing method. Because it forms a solidified pile, it is relatively easy to measure to obtain more accurate radius data. However, this method is difficult to apply to the test of the diffusion radius of the remediation agent based on water solubility.

In the in-situ remediation process of injection wells, the empirical method is also used to design the diffusion radius of the agent. For the complicated hydrogeological conditions, the contaminated site does not pass the field test to determine the effective diffusion radius parameters, which has greater blindness. The injection well itself has poor adaptability to the clay layer, and it also limits its application in clay-based sites. The low injection pressure is difficult to apply methods such as observation.

The physicochemical properties of the tracer and its interaction with the injected agent and soil/groundwater contaminants will directly affect the flow characteristics of the tracer. It is directly related to whether the tracer can track the injected fluid, feedback the flow characteristics of the injected fluid, and have an impact on the final interpretation. Since most of the remediation agents are water-soluble substances, they are easily injected into the soil and groundwater environment, and chemically or biologically react with the contaminants. Currently used tracers can be divided into five categories: water-soluble chemical tracers, water-soluble radiotracers, gas tracers, non-radioactive isotope tracers, stable isotope tracers. The domestic Air Sparging remediation uses acetylene gas tracer to study the flow pattern distribution of Air Sparging (AS), which has greater sensitivity and accuracy than the dissolved oxygen method. However, the method is suitable for the diffusion of gaseous medium in soil and groundwater, and the application range is narrow.

Chinese invention patent of "Method for determining diameter of high-pressure jet grouting pile based on circular free turbulent jet theory" with application number 201110314616.2 discloses a method for determining the radius of a solidified body of a high-pressure rotary jet foundation reinforcement construction, which determines the diameter of the solidified pile according to the critical failure rate of the soil layer, the flow rate of the cement slurry at the exit of the nozzle, and the decay coefficient along the spray distance. This method is improved compared with the empirical method, but it still cannot solve the problem of the penetration diffusion radius of the remediation agent under high pressure injection conditions.

An agent injection points distribution method proposed by Chinese invention patent No. 201510159423.2 "A method for in-situ remediation of chromium contamination", does not consider the influence of groundwater flow, and the engineering construction is poor in operability. In addition, the in-situ remediation method of the invention has the disadvantage that the holes distribution method does not consider the influence of the groundwater flow during the effective reaction period of the remediation agent according to the difference in the permeability of the soil layer, and the overlapping area is too large and uneconomical.

Using the foreign Geoprobe platform and its direct-push fixed-depth quick-sampling system has the following characteristics: the technology is mature and stable, the pipe diameter is small, the accessories can be reused after washing, the cost is low, the disturbance to the formation is small, the sampling efficiency and the resolution are high, and the true and accurate tracer data capture is facilitated. The traditional hollow auger or prepacked monitoring well is set up, which takes a long time, high cost, large pipe diameter, requires packing operation, and has large disturbance to the ground layer, which is not conducive to obtaining true and accurate tracer data capture.

Sampling by mechanical bladder pump with manual operation requires low cost, has secondary filtration of the pump body with screen, small disturbance, is easy to obtain representative samples; sampling by the small stainless steel belle tube has large disturbance, and there is no secondary screen filtration, and the sample is easy to be turbid; in addition, the slow washing well sampling has complex system, requires electric drive, and the installation is cumbersome, the cost is high and uneconomical.

In Chinese invention patent application for "a chrome-contaminated in-situ remediation method" of application number 201510159423.2, the injection method is single tube method, the pressure of the grouting pump is low, and the distribution is only uniform in the crack. There are disadvantages such as small volume of the agent dispensing station and low injection efficiency, and the stability of the effective diffusion radius data is poor.

SUMMARY OF THE INVENTION

The purpose of the present invention is to solve the problem of determining the effective diffusion radius of the agent and optimizing the holes parameters in the design of the existing in-situ injection remediation system, to solve the problem that most of the current empirical methods to determine the effective diffusion radius of the agent is less accurate, and the effect of groundwater flow on the diffusion of the agent during the effective reaction cycle of the agent is not considered, resulting in waste of mechanical costs. A method for determining the diffusion radius of in-situ injection and remediation of contaminated soil and groundwater is further provided.

The object of the present is realized by the following technical schemes:

A method for determining the diffusion radius of in-situ injection and remediation of contaminated soil and groundwater, realized by the following steps:

step one: distributing and guided-boring:

the in-situ injection holes distribution parameters satisfies the following formula:

$$L=1.73R_0 \quad (1)$$

$$B=1.50R_0+B_1 \quad (2)$$

$$v=KI \quad (3)$$

$$B_1=vt \quad (4)$$

wherein L—the optimal hole spacing of the in-situ injection point, perpendicular to the groundwater flow direction; B—the optimal row spacing of in-situ injection point, along the groundwater flow direction; $R_0$—effective diffusion radius of the agent in the aquifer under high pressure injection conditions, unit: m; K—permeability coefficient of aquifer, unit: m/d; I—hydraulic gradient of groundwater; v—flow rate of groundwater, unit: m/d; t—effective reaction time of the agent in groundwater, unit: d; $B_1$—flow distance of the agent in groundwater during the effective reaction time, unit: m.

The in-situ injection has a total of three groups of test holes, the holes distribution parameters of group I: R1, L1, B1; the holes distribution parameters of group II: R2, L2, B2; the holes distribution parameters of group III: R3, L3, B3, wherein the two groups share two injection points, for a total of 10 injection points.

The guided-boring adopts a percussion-rotary drilling method of using a pneumatic air DTH hammer, for leading the hole to the hard layer of the miscellaneous fill layer or the original building foundation, then 10 in-situ injection points (drilling holes) are completed in sequence, that is, three groups of test points with the depth of the guided-boring being about 3 m.

Step two: remediation agent preparation: the sodium bromide is selected as a tracer, added to a typical concentration of remediation agent solution/slurry in a certain proportion, and injected it into the target aquifer in high pressure injection process; the preparation concentration of bromide ions and the dosage way: the mass ratio of the remediation agent to the tracer is: the remediation agent: sodium bromide=100~150:1, and the initial concentration of sodium bromide is 300~700 mg/L.

Step three: in situ injection of the remediation agent: using gas and liquid double pipe method, the injection pressure parameter of the remediation agent liquid flow is 25~30 Mpa, and the injection pressure parameter of the compressed air is 0.7~0.8 Mpa; the remediation agent is injected into the soil and groundwater while being prepared with the bromide ion to be a solution.

a) Agent injection at the injection points of Group I: during the injection process, the slurry-returning at the first hole of the group is observed, and the construction of the remaining adjacent holes requires simultaneous observation of the slurry-channeling and the slurry return;

b) agent injection at the injection points of Group II: during the injection process, one hole of Group I is used, and the construction of the remaining three adjacent holes requires simultaneous observation of the slurry-channeling and the slurry return of adjacent holes;

c) agent injection at the injection points of Group III: one hole of Group II is used, and the construction of the remaining three adjacent holes requires simultaneous observation of the slurry-channeling and the slurry return of adjacent holes.

Step four: the determination for the injection process through observation method:

a) test of Group I: determining initially whether the R value is too small by judging whether there are serious slurry-channeling and slurry-returning;

b) test of Group II: determining initially whether the R value is too large by judging whether there are no serious slurry-channeling and slurry-returning;

c) test of Group III: determining initially whether the R value is reasonable by judging whether there are less serious slurry-channeling and slurry-returning;

the conclusion is that the diffusion radius of the Nth group (N=1, 2, 3) is reasonable, therefore, the Nth group is selected as the focus of the tracer monitoring sampling point.

Step five: monitoring and detection of bromide ions in groundwater: the monitoring point of bromide ion concentration is mainly placed in the test group where $R_0$ is more reasonable while considering porous effects such as single hole, double holes, and triple holes, the selection of monitoring points being C1, C2, C3, C4, C5; after all injection points have completed the injection of the agent for 24 hours, the groundwater samples are rapidly collected using a fixed depth quick-sampling system, promptly sent to a third-party laboratory to detect the concentration of bromide ions in groundwater while quickly testing the samples to be tested on the retained site; the quick fixed-depth sampling system method described above uses a Geoprobe rig to press a 2.25-inch steel casing with a disposable drill bit at the bottom, and a steel screen tube with a length of 1.5 m and an outer diameter of 1.25 inches into the groundwater aquifer at a predetermined depth before lifting the outer casing directly, and the internal steel screen tube is set in the designed sampling depth of the bromide ion in the groundwater, then the mechanical ground bladder pump is used to quickly collect representative groundwater samples after the transfer.

Step six: on-site rapid detection for tracer: the collected groundwater sample is rapidly detected by the pH/ion concentration detector for the concentration of bromide ions in the groundwater at the bromide concentration monitoring points. The test conditions are: BR502 bromine electrode; 100 mL of bromide standard solution, 30 mL of reference electrode solution, ionic strength regulator Measuring range: 0.4~7990 mg/L, pH range 2~11, solution temperature range 5~40° C.

Step seven: determination through tracer method: all bromide monitoring points, background value rapid test data and third-party laboratory test data are analyzed, and whether the distance from the injection point represented by the measured sample is within the effective diffusion radius is determined according to whether the concentration of the bromide ion in the sample is greater than the background value; the distance corresponding to the point where the concentration exceeds 50% of the background value is defined as the effective diffusion radius; the tracer determination method is mainly based on on-site rapid data, uses the third-party laboratory data as a test and review of on-site rapid test data.

Step eight: comprehensively determination through the observation method combined with the bromide ion tracer method: the reasonable range of $R_0$ initially determined by the observation method, and the distance corresponding to the point where the concentration of the bromide ion tracer significantly exceeds the background value is the precise range of $R_0$, finally, the three groups of tests are determined by the observation method+tracer method to determine the optimal $R_0$ for the diffusion of the aquifer, then the smaller value is taken as the engineering recommendation data in consideration of the fact that the formation partially contains interlayers and uneven factors as such.

The beneficial effects of the present invention are:

1. The method of the present invention is suitable for determining and optimizing the effective diffusion radius of the in-situ injection remediation agent of the soil and groundwater (aquifer) in the shallow groundwater-rich site, and a reasonable diffusion radius design is beneficial to solve the problem of slurry-returning.

2. The points distribution of the present invention adopts triangular points distribution, and the row spacing and hole spacing design improves the operability of the engineering construction. Considering the difference in permeability of the remediation medium in the remediation site, the row spacing design parameters consider the diffusion effect of the remediation agent on the groundwater flow during the effective existence period of the underground environment, such as the groundwater flow in the high permeability formation such as sand. The low permeability formation such as clay layer does not consider the influence of groundwater flow, and the holes spacing design does not consider the influence of groundwater flow.

3. The present invention adopts various methods and methods such as observation method+on-site tracer method, on-site rapid test+laboratory test, and the like, so that the accuracy and differential analysis of the parameters obtained is ensured. Among them, the bromide ion electrode method is convenient and fast. The ten round tracer method is designed in three groups of tests, each group consisting of 4 rounds, and the three groups of tests share 2 rounds, which meet the test requirements while saving test time and cost.

4. The tracer method selects bromide ions with better water solubility as tracers. On the one hand, it considers the safety and environmental protection factors. On the other hand, it considers that the bromide ion does not react with the remediation agent and the target contaminant, and may be configured as a uniform solution/slurry with the remediation agent while the diffusion of the tracer in the soil and groundwater being a good representation of the diffusion of the remediation agent after injection into the ground. Therefore, the diffusion law of bromide ions in the aquifer is the diffusion law of the remediation agent, which ensures that the effective diffusion radius obtained is accurate and reliable.

5. Test the diffusion effect after in-situ injection, groundwater sampling adopts direct-push fixed-depth quick-sampling, which has the following characteristics: the technology is mature and stable, the pipe diameter is small, the accessories can be reused after washing, the cost is low, the disturbance to the formation is small, the sampling efficiency and the resolution are high, and the true and accurate tracer data capture is facilitated.

Figure 2:
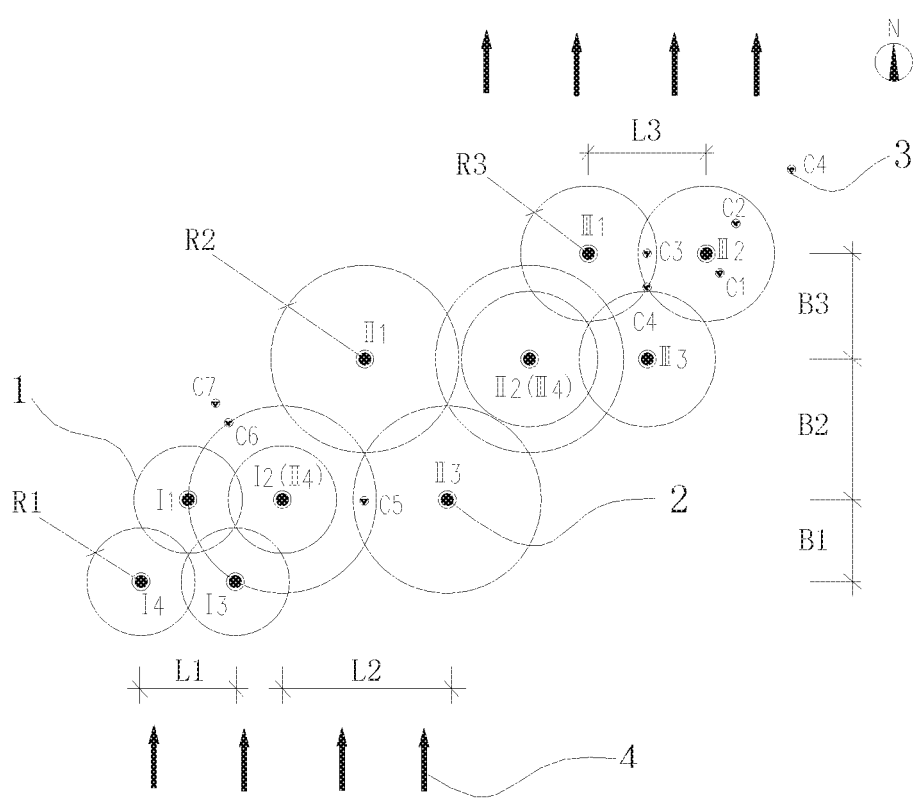
FIG. 2 is a view showing the points distribution of the ten round tracer method of the present invention.

The reference numerals in FIG. 2: 1—injection points agent diffusion radius (R1, R2, R3), 2—in-situ injection points (drilling holes) center, 3—groundwater tracer monitoring points (C1~C7), 4—groundwater flow direction. Test holes in Group I: I1, I2 (II4), I3, I4; Test holes in Group II: II1, II2 (III4), II3, II4; Test holes in Group III: III1, III2, III3, II2 (III4). The holes distribution parameters of Group I: R1, L1, B1; The holes distribution parameters of Group II: R2, L2, B2; The holes distribution parameters of Group III: R3, L3, B3.

Figure 3:
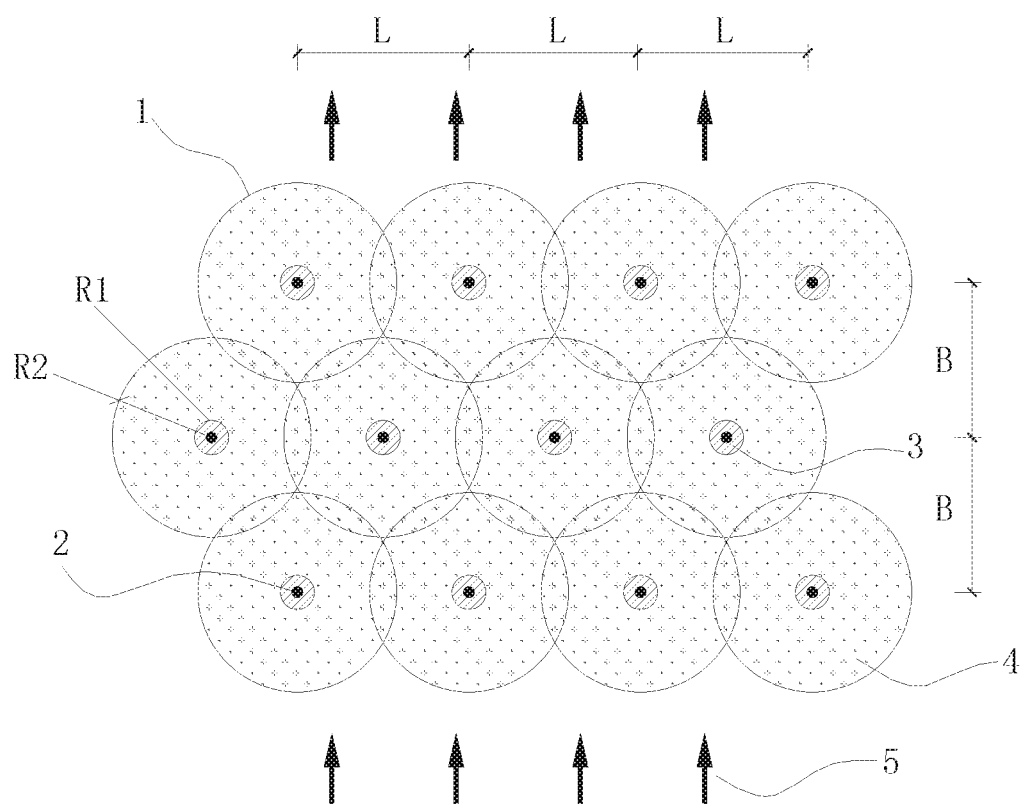
FIG. 3 is a view showing the in-situ injection points distribution of the sand layer site (in consideration of the influence of groundwater on the diffusion of the agent) in Embodiment 2 of the present invention.

The reference numerals in FIG. 3: 1—injection point agent diffusion radius (R), 2—in-situ injection point (drilling) center, 3—high pressure jet mixing area, 4—agent penetration diffusion area, L—hole spacing of sand layer, B—row spacing of sand layer, R1—high pressure jet mixing radius, R2—effective agent diffusion radius of sand layer (including mixing and penetration).

Figure 4:
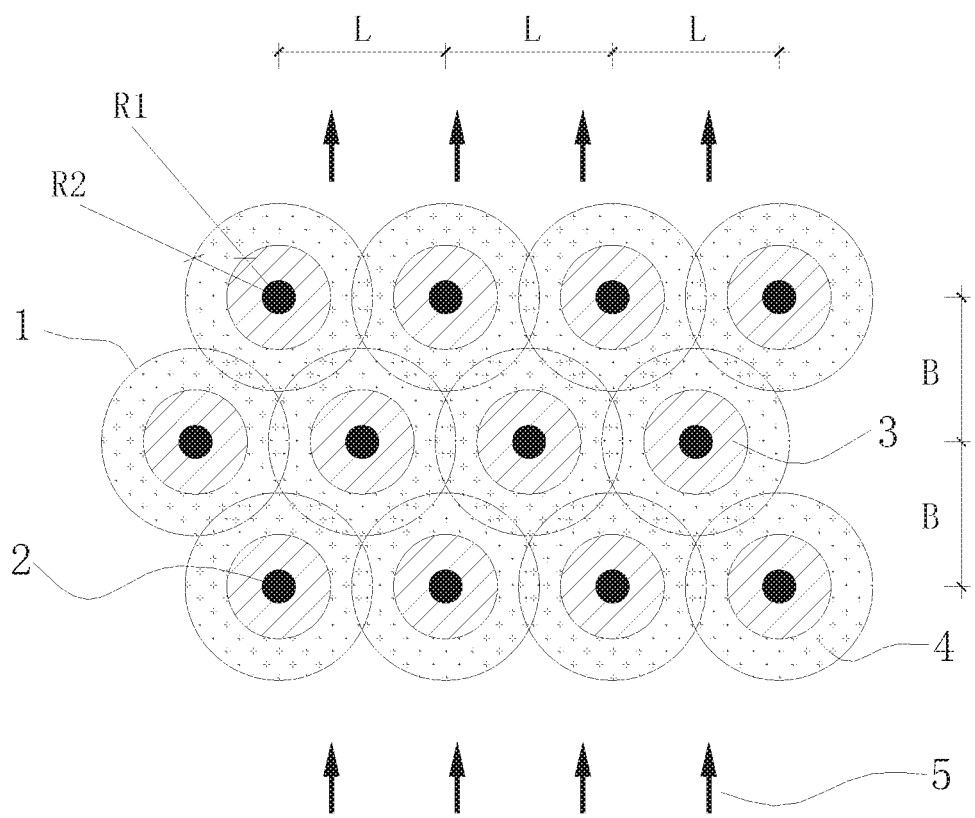
FIG. 4 is a view showing the in-situ injection points distribution of the clay layer site (without consideration of the influence of groundwater on the diffusion of the agent) in Embodiment 2 of the present invention.

The reference numerals in FIG. 4: 1—injection points agent diffusion radius (R), 2—in-situ injection points (drilling holes) center, 3—high pressure jet mixing area, 4—agent penetration diffusion area, L—holes spacing of clay layer, B—row spacing of sand layer, R1—high pressure jet mixing area radius, R2—effective agent diffusion radius of lay layer (including mixing and penetration).

EMBODIMENTS OF THE INVENTION

The present invention will be further described in detail below with reference to the accompanying drawings. This embodiment is implemented on the premise of the technical solution of the present invention, and the detailed embodiment is given, but the scope of protection of the present invention is not limited to the following embodiments.

A shown in FIGS. 1 to 5, the present embodiment relates to a method for determining the diffusion radius of in-situ injection and remediation of contaminated soil and groundwater comprising the following steps:

step one: distributing and guided-boring:
the in-situ injection holes distribution parameter satisfies the following formula:

$$L=1.73R_0 \quad (1)$$

$$B=1.50R_0+B_1 \quad (2)$$

$$v=KI \quad (3)$$

$$B_1=vt \quad (4)$$

wherein L—the optimal holes spacing of the in-situ injection points, perpendicular to the groundwater flow direction; B—the optimal row spacing of in-situ injection points, along the groundwater flow direction; $R_0$—effective diffusion radius of the agent in the aquifer under high pressure injection conditions, unit: m; K—permeability coefficient of aquifer, unit: m/d; I—hydraulic gradient of groundwater; v—flow rate of groundwater, unit: m/d; t—effective reaction time of the agent in groundwater, unit: d; $B_1$—flow distance of the agent in groundwater during the effective reaction time, unit: m.

The in-situ injection has a total of three groups of test holes, the holes distribution parameters of group I: R1, L1, B1; the holes distribution parameters of group II: R2, L2, B2; the holes distribution parameters of group III: R3, L3, B3, wherein the two groups share 2 injection points, for a total of 10 injection points numbered 1~10. Therefore, the present embodiment is also referred to as "ten round tracer method" to determine the diffusion radius of the agent.

The guided-boring adopts a method of using a pneumatic air DTH hammer to impact the rotary drilling, for leading the hole to the hard layer of the miscellaneous fill layer or the original building foundation, then 10 in-situ injection points (drilling holes) are completed in sequence, that is, three groups of test points with the depth of the guided-boring being about 3 m.

Step two: remediation agent preparation: the sodium bromide is selected as a tracer, added to a typical concentration of remediation agent solution/slurry in a certain proportion, and injected it into the target aquifer (contaminated area) in high pressure injection process. The preparation concentration of bromide ions and the dosage way: the mass ratio of the remediation agent to the tracer is: the remediation agent:sodium bromide=100~150:1, and the initial concentration of sodium bromide is 300~700 mg/L.

Step three: in situ injection of the remediation agent (high pressure injection): using gas (compressed air) and liquid (remediation agent solution/slurry) double pipe method, the injection pressure parameter of the remediation agent liquid flow (high pressure grout pump) is 25~30 Mpa, and the injection pressure parameter of the compressed air (air pump) is 0.7~0.8 Mpa. The remediation agent is injected into the soil and groundwater while being prepared with the bromide ion to be a solution.

a) Agent injection at the injection points of Group I (4 holes): during the injection process, the slurry-returning at the first hole of the group is observed, and the construction of the remaining adjacent holes requires simultaneous observation of the slurry-channeling and the slurry return;

b) agent injection at the injection point of Group II (3 holes): during the injection process, one hole of Group I is used, and the construction of the remaining three adjacent holes requires simultaneous observation of the slurry-channeling and the slurry return of adjacent holes;

c) agent injection at the injection point of Group III (3 holes): one hole of Group II is used, and the construction of the remaining three adjacent holes requires simultaneous observation of the slurry-channeling and the slurry return of adjacent holes.

Step four: the determination for the injection process through observation method:

a) test of Group I: determining initially whether the R value is too small by judging whether there are serious slurry-channeling and slurry-returning;

b) test of Group II: determining initially whether the R value is too large by judging whether there are no serious slurry-channeling and slurry-returning;

c) test of Group III: determining initially whether the R value is reasonable by judging whether there are less serious slurry-channeling and slurry-returning.

the conclusion is that the diffusion radius of the Nth group (N=1, 2, 3) is reasonable, therefore, the Nth group is selected as the focus of the tracer monitoring sampling point.

Step five: monitoring and detection of bromide ions in groundwater: the monitoring points of bromide ion concentration is mainly placed in the test group where $R_0$ is more reasonable while considering porous effects such as single hole, double holes, and triple holes, the selection of monitoring points being C1, C2 (double hole), C3 (triple hole), C4 (single hole), C5 (background value). After all injection points have completed the injection of the agent for 24 hours, the groundwater samples are rapidly collected using a fixed depth quick-sampling system (those that are far from the center of the injection points as the bromide ion background value), promptly sent to a third-party laboratory to detect the concentration of bromide ions in groundwater (samples may also be sampled in advance, but the sampling point setting must not be within the radius of influence of the in-situ injection point test to prevent the accuracy and representativeness of the test from being caused by short-circuit) while quickly testing the samples to be tested on the retained site. The quick fixed-depth sampling system method described above uses a Geoprobe rig to press a 2.25-inch steel casing with a disposable drill bit at the bottom, and a steel screen tube with a length of 1.5 m and an outer diameter of 1.25 inches into the groundwater aquifer at a predetermined depth before lifting the outer casing directly, and the internal steel screen tube is set in the designed sampling depth of the bromide ion in the groundwater, then the mechanical ground bladder pump is used to quickly collect representative groundwater samples after the transfer.

Step six: on-site rapid detection for tracer: the collected groundwater sample is rapidly detected by the pH/ion concentration detector for the concentration of bromide ions in the groundwater at the bromide concentration monitoring points. The test conditions are: BR502 bromine electrode; 100 mL of bromide standard solution, 30 mL of reference electrode solution, ionic strength regulator Measuring range: 0.4~7990 mg/L, pH range 2~11, solution temperature range 5~40° C.

Step seven: determination through tracer method: all bromide monitoring points, background value rapid test data and third-party laboratory test data are analyzed, and whether the distance from the injection point represented by the measured sample is within the effective diffusion radius is determined according to whether the concentration of the bromide ion in the sample is greater than the background value. The distance corresponding to the points where the concentration exceeds 50% of the background value is defined as the effective diffusion radius. The tracer determination method is mainly based on on-site rapid data, uses the third-party laboratory data as a test and review of on-site rapid test data.

Step eight: comprehensively determination through the observation method combined with the bromide ion tracer method: the reasonable range of $R_0$ initially determined by the observation method, and the distance corresponding to the point where the concentration of the bromide ion tracer significantly exceeds the background value is the precise range of $R_0$ (if exceeding more than 50% of the background value), finally, the three groups of tests are determined by the observation method+tracer method to determine the optimal $R_0$ for the diffusion of the aquifer, then the smaller value is suggested to be taken as the engineering recommendation data in consideration of the fact that the formation partially contains interlayers and uneven factors as such.

In step one, the holes distribution density (hole/100 m²) of the in-situ injection is determined by the diffusion radius and the holes distribution pattern while being affected by the shape of the boundary of the remedied area. The holes distribution density range for clay (such as silty clay) being 45~46.5 holes/100 m² (the diffusion radius is 0.9 m); the holes distribution density range for sand (such as fine sand) being 4~5 holes/100 m² (the diffusion radius is 2.9 m).

Embodiment 1

The present embodiment is an on-site test method for determining the effective diffusion radius of an organic contaminated soil and a groundwater remediation project by using an in-situ chemical oxidation in-situ injection method. The operations not specifically described in the present embodiment are carried out in accordance with the methods already given in the Summary of the Invention.

Figure 1:
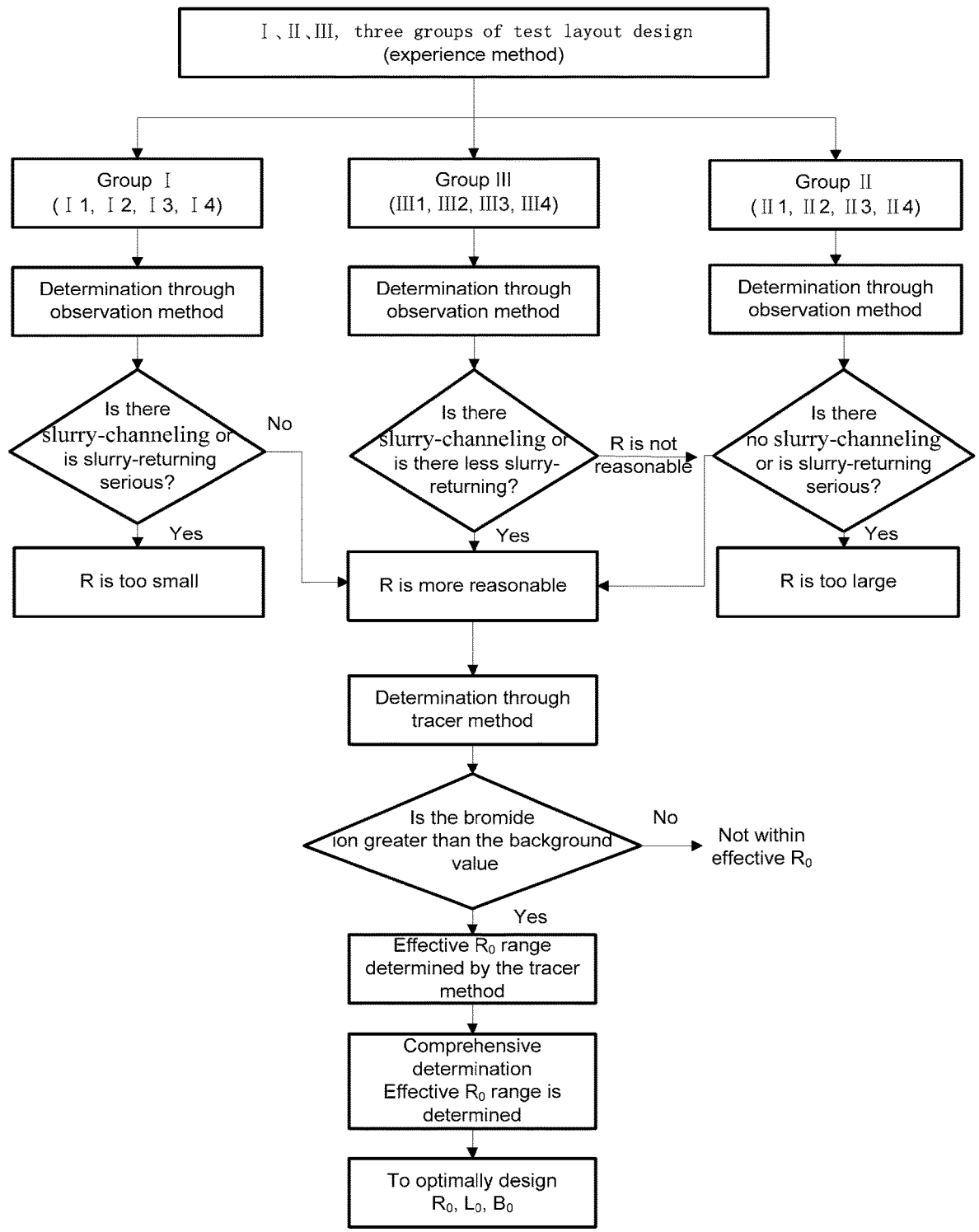
FIG. 1 is a block view showing the flow of determining the diffusion radius of the agent under high pressure injection conditions of soil/groundwater according to the present invention (ten round tracer method).
Figure 5:
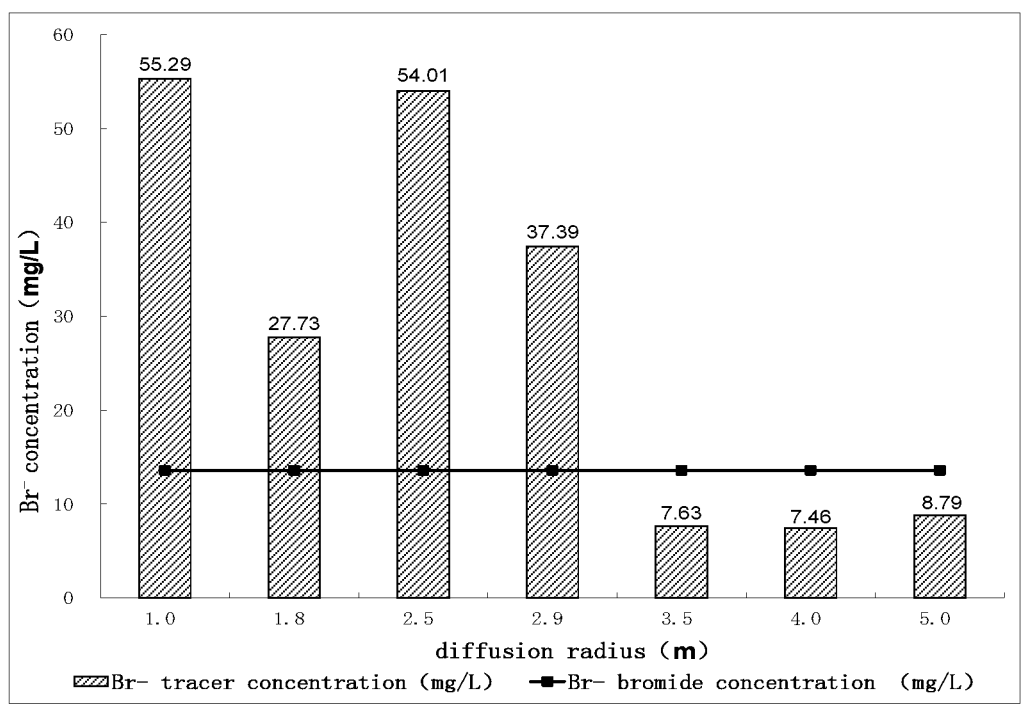
FIG. 5 is a view showing the diffusion law of the tracer in groundwater under the high pressure injection condition of Embodiment 1.

This project is a soil and groundwater remediation project of a chemical plant in Nanjing. The maximum remediation depth of the soil in this site is 12 m. There are two layers of silty clay layer and the aquifer is fine sand layer (distributed at 3~6 m or 4~7 m). The groundwater is shallow (about 1 m) and rich. The target contaminants in soil and groundwater are VOCs/SVOCs organic substances such as chlorobenzene, benzene, and P/O-nitrochlorobenzene. One of the difficulties in in-situ remediation of this project is the lack of practical experience and design basis for the diffusion radius of major strata such as aquifer (fine sand layer) and silty clay layer. This is also the primary problem solved by in-situ chemical oxidation in-situ injection remediation engineering design. The factors affecting the diffusion radius of the agent mainly include injection conditions (such as injection method, pressure), types of remediation agents (such as clay slurry), and grouting amount. The test area is remedied with a target layer of 3~6 m, the groundwater level is 1 m, and the remediation agent uses a water-soluble persulfate and liquid alkali activation solution. Steps for in-situ chemical oxidation in-situ injection—high pressure rotary jet injection tracer test to obtain the diffusion radius of the aquifer (fine sand) are shown in FIGS. 1, 2, 5, briefly described as follows:

(1) distributing and guided-boring: the holes distribution parameters are L, B, wherein L—the optimal holes spacing of the in-situ injection points along the east-west direction (perpendicular to the groundwater flow direction); B—the optimal row spacing of in-situ injection points along the south-north direction (the groundwater flow direction);

the effective reaction time of the agent is t, wherein t—the effective reaction time of the agent in the groundwater, is considered according to the reaction of 20 days (d).

The in-situ injection has a total of three groups of test holes, the holes distribution parameters of group I: R1=2.3 m, L1=4.0 m, B1=3.5 m; the holes distribution parameters of group II: R2=4.0 m, L2=7.0 m, B2=6.0 m; the holes distribution parameters of group III: R3=2.9 m, L3=5.0 m, B3=4.5 m, wherein the two groups share two injection points, for a total of 10 injection points (the number is shown in FIG. 2). Each group of tests consists of two pairs of triangles, and the test simulates the effects of the multi-holes effect of the actual construction. Two of the drilling holes are reused, which achieves the test effect while saving test costs and solving rapid test problems on site.

10 in-situ injection points (drilling holes) are completed in sequence for guided-boring, that is, three groups of test points with the depth of the guided-boring being about 3 m.

(2) Preparation of remediation agent and tracer solution:

6 kg of sodium bromide solid is added to each 3 cubic metre of oxidant (persulfate) and its activator (liquid base) solution to prepare a uniform solution. The remediation agent and the tracer are fully stirred and then injected into the soil and groundwater.

(3) High pressure rotary injection in situ injection: the high pressure injection operations for three groups of test points (10 holes in total) are completed in sequence, and the depth of the rotary jet injection is in the range of 3 to 6 m of aquifer (fine sand). During the injection of each group of tests, it is necessary to observe the slurry-channeling and the slurry-returning at the injection points.

(4) Initially determination for the effective diffusion radius range through observation method: as shown in FIG. 1, the conclusion is that the diffusion radius of Group III is reasonable, therefore, Group III is selected as the focus of the tracer monitoring sampling points.

(5) Tracer monitoring points layout and groundwater quick fixed-depth monitoring sampling: the tracer concentration monitoring points (including the background value point) is set up 24 hours after the completion of the agent injection. The principle of points distribution is: according to the single hole effect, double holes superposition effect and three holes superposition effect of different diffusion rad II, the groundwater samples are collected rapidly. The rapid sampling depth of groundwater is 4.0~5.5 m. As shown in FIG. 2, the selection of monitoring points are C1, C2 (double holes), C3 (triple holes), C4 (single holes), C5 (background value), C6 (background value), C7 (background value).

(6) Tracer on-site quick detection: the MP523 type pH/ion concentration meter is used to quickly test the concentration of bromide ions in the groundwater at the above monitoring points. Before the test, the bromide ion background value of the soil and groundwater in the site is investigated. The background value of bromide ion in groundwater is low (between 10 and 15 mg/L).

(7) Determination through tracer method: according to the literature, when sodium bromide is used as a tracer, the lowest detection limit is 1.0 mg/L, and the recommended maximum ground extraction concentration is 35~50 mg/L. The on-site quick test data of bromide ions in the groundwater area is basically consistent with the literature.

The analysis of the diffusion radius results under high pressure injection construction conditions is shown in Table 1—Diffusion radius results analysis table.

TABLE 1

Diffusion radius results analysis table

| Test Area | Research method | Diffusion radius data obtained (m) | Diffusion radius Recommended value (m) | Corresponding holes distribution method | Remarks |
|---|---|---|---|---|---|
| Aquifer Area | Observation method Tracer test method | 2.5 < R2 < 3.5 2.9~3.2 | 2.9 | Method 2 | The slurry-channeling occurs in the holes spacing of 4 m and 5 m; Group III is the optimal holes distribution method. |

From the above table and FIG. 5, it can be concluded that: observation method, 2.5<R0<3.5; tracer test, 2.9<R0<3.2; the comprehensive value of R0 is 2.9 m, which is reasonable as the engineering recommended data for the aquifer (fine sand) formation. The remediation effect shows that the resulting diffusion radius data is reasonable and economical.

In the same way, the effective diffusion radius of the silty clay layer may be obtained: 0.8~0.9 m, and it is recommended to take 0.9 m.

Embodiment 2

As shown in FIGS. 3 and 4, the present embodiment is an optimization process for in-situ injection of remediation holes distribution parameters of soil and groundwater. This is a process for optimizing the holes distribution parameters, based on the factors such as the groundwater flow at the remediation site, the difference in the permeability of the soil layer, and the effective reaction time of the remediation agent, in the case where the effective diffusion radius is obtained in Embodiment 1. Briefly read as follows:

In Embodiment 1, the recommended values of the effective diffusion radius of two typical soil layers are obtained. R0 for sands (such as fine sand aquifer) is 2.9 m, and $R_0$ for clays (such as silty clay) is 0.9 m. The holes distribution method is a triangle method, and holes distribution method 1 is for sands. Considering the influence of groundwater flow on the row spacing of the holes distribution parameters, the row spacing increases the effective reaction time of the agent (for example, the effective reaction time of the oxidant persulfate in groundwater is about 20 days). The effective diffusion radius of this holes distribution method is much larger than the radius of the rotary jet mixing area. The holes distribution method 2: due to the poor permeability of the clay, the holes spacing and the row spacing of the holes distribution parameters do not consider the influence of groundwater flow. The optimized calculation process is detailed in Table 2—Holes distribution parameter optimized calculation table. After the calculation value is optimized, the final engineering design parameter is obtained by fine adjustment.

The holes distribution density (holes/100 $m^2$) of the in-situ injection is mainly determined by the diffusion radius and the holes distribution pattern while being affected by the shape of the boundary of the remedied area. After the optimization of the in-situ injection holes distribution parameters in the present embodiment, the in-situ remediation mechanical cost may be quickly estimated from the holes distribution density parameters, and the utility is strong. The holes distribution density range for clay (such as silty clay) being 45~46.5 holes/100 $m^2$ (the diffusion radius is 0.9 m); the hole distribution density range for sand (such as fine sand) being 4~5 holes/100 $m^2$ (the diffusion radius is 2.9 m). Therefore, the economics of in-situ injection technology is shown to be significantly better than that for clays.

TABLE 2

Hole distribution parameter optimized calculation table

| Serial number | Holes distribution method | Target layer lithology | Diffusion radius $R_0$(m) | Calculation value for holes spacing L (m) |
|---|---|---|---|---|
| 1 | Method 1 | fine sand | 2.9 | 5.02 |
| 2 | Method 2 | silty clay | 0.9 | 1.56 |

| Serial number | Calculation value for row spacing B (m) | Distance $B_1$ along groundwater flow direction (m) | Design value of holes spacing L (m) | Design value of row spacing B (m) | Remarks |
|---|---|---|---|---|---|
| 1 | 4.56 | 0.21 | 5.00 | 4.50 | Considering the influence of groundwater flow |
| 2 | 1.35 | / | 1.60 | 1.40 | Not considering groundwater flow |

Note:
aquifer K = 4.32 m/d, hydraulic gradient 3‰.

The above is only a preferred embodiment of the present invention, and these specific embodiments are based on different implementations under the overall concept of the present invention, and do not limit the protection scope of the present invention, and anyone skilled in the art may easily think of mortifications and alternations within the technical scope disclosed by the present invention, all of which should be contained within the protection scope of the present invention. Therefore, the scope of the present invention should be determined by the scope of the claims.

The invention claimed is:
1. A method for determining a diffusion radius of in-situ injection and remediation of contaminated soil and groundwater, comprising, step one: distributing and guided-boring in-situ injection holes:
distribution parameters of the in-situ injection holes satisfy the following formula:

$$L=1.73R_0 \quad (1)$$

$$B=1.50R_0+B_1 \quad (2)$$

$$v=KI \quad (3)$$

$$B_1=vt \quad (4)$$

wherein L—optimal holes spacing of the in-situ injection holes, perpendicular to groundwater flow direction; B—optimal row spacing of the in-situ injection holes, along the groundwater flow direction; $R_0$—effective diffusion radius of an agent in an aquifer under high pressure injection conditions, unit: m; K—permeability coefficient of the aquifer, unit: m/d; I—hydraulic gradient of groundwater; v—flow rate of groundwater, unit: m/d; t—effective reaction time of the agent in groundwater, unit: d; $B_1$—flow distance of the agent in groundwater during an effective reaction time, unit: m; wherein d is day, wherein the aquifer is part of groundwater site, and the agent is a liquid to be injected in the in-situ injection holes;
the in-situ injection has a total of three groups of the in-situ injection holes, there are a total of 10 of the in-situ injection holes, the in-situ injection holes distribution parameters of Group I: R1, L1, B1; the in-situ injection holes distribution parameters of Group II: R2, L2, B2; the in-situ injection holes distribution parameters of Group III: R3, L3, B3, wherein Group I and Group II share one of the in-situ injection holes, Group II and Group III share an other one of the in-situ injection hole;
the guided-boring adopts a percussion-rotary drilling method of using a pneumatic air DTH hammer, for leading the in-situ injection holes to a hard layer of a miscellaneous fill layer or an original building foundation, then the 10 in-situ injection holes are completed in sequence, that is, the three groups of the in-situ injection holes have a depth of 3 m;
step two: remediation agent preparation: sodium bromide is selected as a tracer, added to a concentration of a remediation agent solution/slurry in a proportion, and injected it into the aquifer in a pressure injection process; wherein a mass ratio of the remediation agent to the tracer is: the remediation agent: sodium bromide=100~150:1, and an initial concentration of sodium bromide is 300~700 mg/L;
step three: in situ injection of the remediation agent: using gas and liquid double pipe method, an injection pressure of remediation agent is 25~30 Mpa, and an injection pressure of compressed air is 0.7~0.8 Mpa; the remediation agent is injected into the soil and groundwater while being prepared with the bromide ion to be a solution;
a) agent injection at the in-situ injection holes of Group I: during the injection process, slurry-returning at a first in-situ injection hole of Group I is observed, and construction of remaining adjacent in-situ injection holes requires simultaneous observation of slurry-channeling and slurry-returning;
b) agent injection at the in-situ injection holes of Group II, including the shared in-situ injection hole of Group I: during the injection process, the construction of remaining three adjacent in-situ injection holes, which are not shared with Group I requires simultaneous observation of the slurry-channeling and the slurry-returning of the remaining three adjacent in-situ injection holes;
c) agent injection at the in-situ injection holes of Group III including the shared in-situ injection hole of Group II: the construction of remaining three adjacent in-situ injection holes, which are not shared with Group II, requires simultaneous observation of the slurry-channeling and the slurry returning of the remaining three adjacent in-situ injection holes;
step four: determination for the injection process through observation:
a) test of Group I: determining initially whether an R value is too small by judging whether there are slurry-channeling and slurry-returning above a threshold;
b) test of Group II: determining initially whether the R value is too large by judging whether there are no slurry-channeling and slurry-returning above a threshold;
c) test of Group III: determining initially whether the R value is reasonable by judging whether there are slurry-channeling and slurry-returning below the threshold;
conclusion is that the diffusion radius of an Nth group is reasonable, therefore, the Nth group is selected as a focus of tracer monitoring sampling points;
step five: monitoring and detection of bromide ions in groundwater: a monitoring point of bromide ion concentration is mainly placed in a test group where $R_0$ is more reasonable while considering porous effects of single hole, double holes, and triple holes, selection of monitoring points being C1, C2, C3, C4, C5; after all the in-situ injection holes have been completed the injection of the agent for 24 hours, groundwater samples are rapidly collected using a fixed depth quick-sampling system, promptly sent to a third-party laboratory to detect the concentration of bromide ions in the groundwater samples while testing the groundwater samples on a retained site; the fixed-depth quick-sampling system uses a Geoprobe rig to press a 2.25-inch steel casing with a disposable drill bit at a bottom, and an internal steel screen tube with a length of 1.5 m and an outer diameter of 1.25 inches into the groundwater aquifer at a predetermined depth before lifting an outer casing directly, and the internal steel screen tube is set in a designed sampling depth of the bromide ion in the groundwater, then a mechanical ground bladder pump is used to collect representative groundwater samples after transfer;
step six: on-site rapid detection for tracer: the collected groundwater samples are rapidly detected by a pH/ion concentration detector with a BR502 bromine electrode for the concentration of bromide ions in the groundwater at bromide concentration monitoring points; test conditions are: 100 mL of bromide standard solution, 30 mL of reference electrode solution with ionic strength regulator, measuring range is 0.4~7990 mg/L, pH range is 2~11, solution temperature range is 5-40° C.;

step seven: determination through tracer: all the bromide concentration monitoring points, background value on-site test data and third-party laboratory test data are analyzed, and whether a distance from the in-situ injection holes represented by the measured groundwater samples is within an effective diffusion radius is determined according to whether the concentration of the bromide ion in the sample is greater than the background value; the distance corresponding to a point where the concentration of the bromide ion exceeds 50% of the background value is defined as the effective diffusion radius; the determination through tracer is mainly based on on-site data, using the third-party laboratory data as a test and review of the on-site test data;

step eight: comprehensive determination through the observation combined with the bromide ion tracer determination: a reasonable range of $R_0$ initially determined by the observation, and the distance corresponding to the in-situ injection hole where the concentration of the bromide ion tracer significantly exceeds the background value finally, the three groups of tests are performed by the observation and then the tracer determination is performed to determine an optimal $R_0$ for liquid diffusion in the aquifer, a smaller value of the optimal $R_0$ determined by the observation and the tracer is taken as an engineering recommendation data.

2. The method for determining the diffusion radius of in-situ injection and remediation of contaminated soil and groundwater according to claim 1, wherein in step one, a holes distribution density of the in-situ injection is determined by the diffusion radius and a hole distribution pattern while being affected by a shape of a boundary of an area of land that is affected by the method, the holes distribution density for clay land is 45-46.5 holes/100 $m^2$; the holes distribution density for sand land is 4-5 holes/100 $m^2$.

* * * * *